(12) United States Patent
Ryan et al.

(10) Patent No.: US 7,867,250 B2
(45) Date of Patent: *Jan. 11, 2011

(54) SEPTAL OCCLUDER AND ASSOCIATED METHODS

(75) Inventors: Carol A. Ryan, Topsfield, MA (US); Andrzej J. Chanduszko, Weymouth, MA (US)

(73) Assignee: NMT Medical, Inc., Boston, MA (US)

( * ) Notice: Subject to any disclaimer, the term of this patent is extended or adjusted under 35 U.S.C. 154(b) by 185 days.

This patent is subject to a terminal disclaimer.

(21) Appl. No.: 10/326,535

(22) Filed: Dec. 19, 2002

(65) Prior Publication Data

US 2003/0191495 A1 Oct. 9, 2003

Related U.S. Application Data

(60) Provisional application No. 60/340,858, filed on Dec. 19, 2001.

(51) Int. Cl.
*A61B 17/08* (2006.01)

(52) U.S. Cl. ............... 606/215; 606/213

(58) Field of Classification Search ......... 606/216, 606/213, 215, 200; 602/213, 215
See application file for complete search history.

(56) References Cited

U.S. PATENT DOCUMENTS

| | | | |
|---|---|---|---|
| 3,294,631 A | 12/1973 | Mancusi | |
| 3,824,631 A | 7/1974 | Burstein et al. | |
| 3,874,388 A | 4/1975 | King et al. | 128/334 |
| 3,875,648 A | 4/1975 | Bone | 29/417 |
| 3,924,631 A | 12/1975 | Mancusi, Jr. | |
| 4,006,747 A | 2/1977 | Kronenthal et al. | 128/335 |
| 4,007,743 A | 2/1977 | Blake | 128/334 |
| 4,149,327 A | 4/1979 | Hammer et al. | |
| 4,425,908 A | 1/1984 | Simon | 128/1 |
| 4,610,674 A | 9/1986 | Suzuki et al. | |
| 4,626,245 A | 12/1986 | Weinstein | |
| 4,696,300 A | 9/1987 | Anderson | 128/334 |
| 4,710,192 A | 12/1987 | Liotta et al. | |
| 4,836,204 A | 6/1989 | Landymore et al. | 128/334 |
| 4,840,623 A | 6/1989 | Quackenbush | |
| 4,902,508 A | 2/1990 | Badylak et al. | |
| 4,915,107 A | 4/1990 | Rebuffat et al. | 606/144 |
| 4,917,089 A | 4/1990 | Sideris | |
| 4,956,178 A | 9/1990 | Badylak et al. | |
| 5,021,059 A | 6/1991 | Kensey et al. | 606/213 |

(Continued)

FOREIGN PATENT DOCUMENTS

DE 9413645 U1 10/1994

(Continued)

OTHER PUBLICATIONS

Stöckel, "Nitinol Medical Devices and Implants," SMST-2000 Conference Proceedings, 2001, pp. 531-541.

(Continued)

*Primary Examiner*—Darwin P Erezo
(74) *Attorney, Agent, or Firm*—Helen S. Liu

(57) ABSTRACT

Devices are provided for closing septal defects such as PFOs. The devices generally include a proximal anchor member, a distal anchor member, and a flexible center joint connecting the two anchor members.

84 Claims, 13 Drawing Sheets

U.S. PATENT DOCUMENTS

| | | | |
|---|---|---|---|
| 5,037,433 A | 8/1991 | Wilk et al. ............... 606/139 |
| 5,041,129 A | 8/1991 | Hayhurst et al. ........... 606/232 |
| 5,078,736 A | 1/1992 | Behl |
| 5,106,913 A | 4/1992 | Yamaguchi et al. |
| 5,108,420 A * | 4/1992 | Marks ...................... 606/213 |
| 5,149,327 A | 9/1992 | Oshiyama |
| 5,167,363 A | 12/1992 | Adkinson et al. |
| 5,167,637 A | 12/1992 | Okada et al. |
| 5,171,259 A | 12/1992 | Inoue |
| 5,192,301 A | 3/1993 | Kamiya et al. ............. 606/213 |
| 5,222,974 A | 6/1993 | Kensey et al. ............. 606/213 |
| 5,226,879 A | 7/1993 | Ensminger et al. |
| 5,236,440 A | 8/1993 | Hlavacek .................. 606/219 |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli ............. 128/898 |
| 5,275,826 A | 1/1994 | Badylak et al. |
| 5,282,827 A | 2/1994 | Kensey et al. ............. 606/215 |
| 5,284,488 A | 2/1994 | Sideris ...................... 606/213 |
| 5,304,184 A | 4/1994 | Hathaway et al. ......... 606/144 |
| 5,312,341 A | 5/1994 | Turi |
| 5,312,435 A | 5/1994 | Nash et al. ................. 606/213 |
| 5,316,262 A | 5/1994 | Koebler |
| 5,334,217 A | 8/1994 | Das ............................ 606/213 |
| 5,350,363 A | 9/1994 | Goode et al. |
| 5,350,399 A * | 9/1994 | Erlebacher et al. ........ 606/213 |
| 5,354,308 A | 10/1994 | Simon et al. ............... 606/198 |
| 5,411,481 A | 5/1995 | Allen et al. ................. 606/144 |
| 5,413,584 A | 5/1995 | Schulze ...................... 606/219 |
| 5,417,699 A | 5/1995 | Klein et al. ................. 606/144 |
| 5,425,744 A | 6/1995 | Fagan et al. ................ 606/215 |
| 5,433,727 A | 7/1995 | Sideris ...................... 606/213 |
| 5,451,235 A | 9/1995 | Lock et al. ................. 606/213 |
| 5,478,353 A | 12/1995 | Yoon .......................... 606/213 |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. ................ 623/11 |
| 5,534,432 A | 7/1996 | Peoples et al. |
| 5,540,712 A | 7/1996 | Kleshinski et al. ......... 606/198 |
| 5,562,632 A | 10/1996 | Davila et al. |
| 5,577,299 A | 11/1996 | Thompson et al. |
| 5,601,571 A | 2/1997 | Moss .......................... 606/139 |
| 5,618,311 A | 4/1997 | Gryskiewicz ............... 606/216 |
| 5,620,461 A | 4/1997 | Muijs Van De Moer et al. |
| 5,626,599 A | 5/1997 | Bourne et al. |
| 5,634,936 A | 6/1997 | Linden et al. .............. 606/213 |
| 5,649,950 A | 7/1997 | Bourne et al. |
| 5,649,959 A * | 7/1997 | Hannam et al. ............ 606/213 |
| 5,663,063 A | 9/1997 | Peoples et al. |
| 5,683,411 A | 11/1997 | Kavteladze et al. ........ 606/200 |
| 5,690,674 A * | 11/1997 | Diaz .......................... 606/213 |
| 5,693,085 A | 12/1997 | Buirge et al. |
| 5,702,421 A * | 12/1997 | Schneidt .................... 606/213 |
| 5,709,707 A | 1/1998 | Lock et al. ................. 606/213 |
| 5,717,259 A | 2/1998 | Schexnayder |
| 5,720,754 A | 2/1998 | Middleman et al. ....... 606/127 |
| 5,725,552 A | 3/1998 | Kotula et al. ............... 606/213 |
| 5,733,294 A | 3/1998 | Forber et al. ............... 606/151 |
| 5,733,337 A | 3/1998 | Carr, Jr. et al. |
| 5,741,297 A | 4/1998 | Simon ........................ 606/213 |
| 5,776,162 A | 7/1998 | Kleshinski ................. 606/198 |
| 5,776,183 A | 7/1998 | Kanesaka et al. |
| 5,797,960 A | 8/1998 | Stevens et al. ............. 606/213 |
| 5,800,516 A | 9/1998 | Fine et al. |
| 5,810,884 A | 9/1998 | Kim ............................ 606/213 |
| 5,823,956 A | 10/1998 | Roth et al. .................. 600/374 |
| 5,829,447 A | 11/1998 | Stevens et al. ............. 128/898 |
| 5,853,420 A | 12/1998 | Chevillon et al. |
| 5,853,422 A * | 12/1998 | Huebsch et al. ............ 606/213 |
| 5,855,614 A | 1/1999 | Stevens et al. ............. 623/11 |
| 5,861,003 A | 1/1999 | Latson et al. ............... 606/213 |
| 5,865,791 A | 2/1999 | Whayne et al. |
| 5,879,366 A | 3/1999 | Shaw et al. ................ 606/213 |
| 5,893,856 A | 4/1999 | Jacob et al. ................ 606/151 |
| 5,902,319 A | 5/1999 | Daley ........................ 606/219 |
| 5,904,703 A | 5/1999 | Gilson ...................... 606/213 |
| 5,919,200 A | 7/1999 | Stambaugh et al. ........ 606/159 |
| 5,924,424 A | 7/1999 | Stevens et al. ............. 128/898 |
| 5,928,250 A | 7/1999 | Koike et al. |
| 5,955,110 A | 9/1999 | Patel et al. |
| 5,976,174 A | 11/1999 | Ruiz .......................... 606/213 |
| 5,989,268 A | 11/1999 | Pugsley, Jr. et al. ........ 606/144 |
| 5,993,475 A | 11/1999 | Lin et al. .................... 606/213 |
| 5,993,844 A | 11/1999 | Abraham et al. |
| 5,997,575 A | 12/1999 | Whitson et al. |
| 6,010,517 A | 1/2000 | Baccaro ..................... 606/151 |
| 6,024,756 A | 2/2000 | Huebsch et al. ............ 606/213 |
| 6,030,007 A | 2/2000 | Bassily et al. |
| 6,056,760 A | 5/2000 | Koike et al. ................ 606/148 |
| 6,071,998 A | 6/2000 | Muller et al. |
| 6,077,291 A | 6/2000 | Das ............................ 606/213 |
| 6,077,880 A | 6/2000 | Castillo et al. |
| 6,079,414 A | 6/2000 | Roth .......................... 128/898 |
| 6,080,182 A | 6/2000 | Shaw et al. ................ 606/213 |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. ............ 606/213 |
| 6,126,686 A | 10/2000 | Badylak et al. |
| 6,132,438 A | 10/2000 | Fleischman et al. ........ 606/139 |
| 6,143,037 A | 11/2000 | Goldstein et al. |
| 6,152,144 A | 11/2000 | Lesh et al. |
| 6,165,183 A | 12/2000 | Kuehn et al. ............... 606/139 |
| 6,165,204 A | 12/2000 | Levinson et al. ........... 606/232 |
| 6,171,329 B1 | 1/2001 | Shaw et al. ................ 606/213 |
| 6,174,322 B1 | 1/2001 | Schneidt .................... 606/213 |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson ................... 606/144 |
| 6,206,907 B1 | 3/2001 | Marino et al. .............. 606/215 |
| 6,214,029 B1 * | 4/2001 | Thill et al. .................. 606/213 |
| 6,217,590 B1 | 4/2001 | Levinson ................... 606/142 |
| 6,221,092 B1 | 4/2001 | Koike et al. ................ 606/213 |
| 6,227,139 B1 | 5/2001 | Nguyen et al. |
| 6,228,097 B1 | 5/2001 | Levinson et al. ........... 606/142 |
| 6,231,561 B1 | 5/2001 | Frazier et al. |
| 6,245,080 B1 | 6/2001 | Levinson ................... 606/144 |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. .............. 606/213 |
| 6,277,138 B1 | 8/2001 | Levinson et al. ........... 606/200 |
| 6,277,139 B1 | 8/2001 | Levinson et al. ........... 606/200 |
| 6,287,317 B1 | 9/2001 | Makower et al. ........... 606/153 |
| 6,290,674 B1 | 9/2001 | Roue et al. ................. 604/107 |
| 6,306,150 B1 | 10/2001 | Levinson ................... 606/158 |
| 6,306,424 B1 | 10/2001 | Vyakarnam et al. |
| 6,312,446 B1 | 11/2001 | Huebsch et al. ............ 606/213 |
| 6,316,262 B1 | 11/2001 | Huisman et al. |
| 6,319,263 B1 | 11/2001 | Levinson ................... 606/144 |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. ................ 606/213 |
| 6,344,048 B1 | 2/2002 | Chin et al. |
| 6,344,049 B1 | 2/2002 | Levinson et al. ........... 606/200 |
| 6,346,074 B1 | 2/2002 | Roth |
| 6,348,041 B1 | 2/2002 | Klint .......................... 600/585 |
| 6,352,552 B1 | 3/2002 | Levinson et al. ........... 623/1.15 |
| 6,355,052 B1 | 3/2002 | Neuss et al. ................ 606/213 |
| 6,356,782 B1 | 3/2002 | Sirimanne et al. |

| | | | | | | |
|---|---|---|---|---|---|---|
| 6,364,853 B1 | 4/2002 | French et al. ............... 604/35 | | 2002/0128680 A1 | 9/2002 | Pavlovic |
| 6,371,904 B1 | 4/2002 | Sirimanne et al. | | 2002/0129819 A1 | 9/2002 | Feldman et al. ............ 128/831 |
| 6,375,625 B1 | 4/2002 | French et al. ............... 600/573 | | 2002/0164729 A1 | 11/2002 | Skraly et al. |
| 6,375,671 B1 | 4/2002 | Kobayashi et al. .......... 606/213 | | 2002/0169377 A1 | 11/2002 | Khairkhahan et al. |
| 6,379,342 B1 | 4/2002 | Levinson .................... 604/310 | | 2002/0183786 A1 | 12/2002 | Girton ....................... 606/213 |
| 6,379,368 B1 | 4/2002 | Corcoran et al. ............ 606/153 | | 2002/0183787 A1 | 12/2002 | Wahr et al. ................. 606/213 |
| 6,387,104 B1 | 5/2002 | Pugsley, Jr. et al. ......... 606/139 | | 2002/0183823 A1 | 12/2002 | Pappu |
| 6,398,796 B2 | 6/2002 | Levinson .................... 606/144 | | 2002/0198563 A1 | 12/2002 | Gainor et al. |
| 6,402,772 B1 | 6/2002 | Amplatz et al. | | 2003/0004533 A1 | 1/2003 | Dieck et al. |
| 6,419,669 B1 | 7/2002 | Frazier et al. | | 2003/0023266 A1 | 1/2003 | Welch et al. |
| 6,426,145 B1 | 7/2002 | Moroni | | 2003/0028213 A1* | 2/2003 | Thill et al. .................. 606/200 |
| 6,436,088 B2 | 8/2002 | Frazier et al. | | 2003/0045893 A1 | 3/2003 | Ginn |
| 6,440,152 B1 | 8/2002 | Gainor et al. ............... 606/213 | | 2003/0050665 A1 | 3/2003 | Ginn |
| 6,460,749 B1 | 10/2002 | Levinson et al. .......... 227/180.1 | | 2003/0055455 A1 | 3/2003 | Yang et al. |
| 6,482,224 B1 | 11/2002 | Michler et al. | | 2003/0057156 A1 | 3/2003 | Peterson et al. |
| 6,488,706 B1 | 12/2002 | Solymar ..................... 623/3.1 | | 2003/0059640 A1 | 3/2003 | Marton et al. ............... 428/544 |
| 6,494,888 B1 | 12/2002 | Laufer et al. ............... 606/153 | | 2003/0065379 A1 | 4/2003 | Babbas et al. |
| 6,508,828 B1* | 1/2003 | Akerfeldt et al. ............ 606/215 | | 2003/0100920 A1 | 5/2003 | Akin et al. |
| 6,514,515 B1 | 2/2003 | Williams | | 2003/0120337 A1 | 6/2003 | Van Tassel et al. |
| 6,548,569 B1 | 4/2003 | Williams et al. | | 2003/0139819 A1 | 7/2003 | Beer et al. |
| 6,551,303 B1 | 4/2003 | Van Tassel et al. | | 2003/0171774 A1 | 9/2003 | Freudenthal et al. |
| 6,551,344 B2 | 4/2003 | Thill | | 2003/0191495 A1 | 10/2003 | Ryan et al. |
| 6,585,755 B2 | 7/2003 | Jackson et al. | | 2003/0195530 A1 | 10/2003 | Thill |
| 6,596,013 B2* | 7/2003 | Yang et al. .................. 606/215 | | 2003/0204203 A1 | 10/2003 | Khairkhahan et al. |
| 6,599,448 B1 | 7/2003 | Ehrhard, Jr. et al. | | 2004/0044361 A1 | 3/2004 | Franzier et al. |
| 6,610,764 B1 | 8/2003 | Martin et al. | | 2004/0073242 A1 | 4/2004 | Chanduszko |
| 6,623,508 B2 | 9/2003 | Shaw et al. | | 2004/0176799 A1 | 9/2004 | Chanduszko et al. |
| 6,623,518 B2 | 9/2003 | Thompson et al. | | 2004/0210301 A1 | 10/2004 | Obermiller |
| 6,626,936 B2 | 9/2003 | Stinson | | 2004/0234567 A1 | 11/2004 | Dawson |
| 6,629,901 B2 | 10/2003 | Huang | | 2005/0025809 A1 | 2/2005 | Hasirci et al. |
| 6,666,861 B1 | 12/2003 | Grabek | | 2005/0043759 A1 | 2/2005 | Chanduszko |
| 6,669,722 B2 | 12/2003 | Chen et al. | | 2005/0113868 A1 | 5/2005 | Devellian |
| 6,689,589 B2 | 2/2004 | Huisman et al. | | 2005/0267523 A1 | 12/2005 | Devellian et al. |
| 6,712,804 B2 | 3/2004 | Roue et al. | | 2005/0273135 A1 | 12/2005 | Chanduszko et al. |
| 6,712,836 B1 | 3/2004 | Berg et al. | | 2005/0288786 A1 | 12/2005 | Chanduszko |
| 6,726,696 B1 | 4/2004 | Houser et al. | | 2006/0122647 A1 | 6/2006 | Callaghan et al. |
| 6,828,357 B1 | 12/2004 | Martin et al. | | 2006/0265004 A1 | 11/2006 | Callaghan et al. |
| 6,838,493 B2 | 1/2005 | Williams et al. | | 2007/0010851 A1 | 1/2007 | Chanduszko et al. |
| 6,867,247 B2 | 3/2005 | Williams et al. | | 2007/0167981 A1 | 7/2007 | Opolski |
| 6,867,248 B1 | 3/2005 | Martin et al. | | | | |
| 6,867,249 B2 | 3/2005 | Lee et al. | | FOREIGN PATENT DOCUMENTS | | |
| 6,921,410 B2 | 7/2005 | Porter | | | | |
| 7,318,833 B2* | 1/2008 | Chanduszko ................ 606/215 | | EP | 0362113 | 4/1990 |
| 2001/0010481 A1 | 8/2001 | Blanc et al. | | EP | 0474887 | 3/1992 |
| 2001/0014800 A1 | 8/2001 | Frazier et al. | | EP | 0839549 | 5/1998 |
| 2001/0034537 A1 | 10/2001 | Shaw et al. .................. 606/213 | | EP | 1 013 227 | 6/2000 |
| 2001/0034567 A1 | 10/2001 | Allen et al. | | EP | 1 046 375 | 10/2000 |
| 2001/0037129 A1 | 11/2001 | Thill | | EP | 1 222 897 | 7/2002 |
| 2001/0039435 A1 | 11/2001 | Roue et al. | | WO | WO 96/25179 | 8/1996 |
| 2001/0041914 A1 | 11/2001 | Frazier et al. | | WO | WO 96/31157 | 10/1996 |
| 2001/0041915 A1 | 11/2001 | Roue et al. | | WO | WO-98/07375 | 2/1998 |
| 2001/0044639 A1 | 11/2001 | Levinson .................... 606/228 | | WO | WO-98/08462 | 3/1998 |
| 2001/0049492 A1 | 12/2001 | Frazier et al. ............... 604/104 | | WO | WO-98/16174 | 4/1998 |
| 2002/0010481 A1 | 1/2002 | Jayaraman .................. 606/151 | | WO | WO-98/29026 | 7/1998 |
| 2002/0019648 A1 | 2/2002 | Akerfeldt et al. | | WO | WO-98/51812 | 11/1998 |
| 2002/0026208 A1 | 2/2002 | Roe et al. | | WO | WO-99/05977 | 2/1999 |
| 2002/0029048 A1 | 3/2002 | Miller ........................ 606/138 | | WO | WO-98/18864 | 4/1999 |
| 2002/0032459 A1 | 3/2002 | Horzewski et al. | | WO | WO-99/18862 | 4/1999 |
| 2002/0032462 A1 | 3/2002 | Houser et al. ............... 606/213 | | WO | WO-99/18864 | 4/1999 |
| 2002/0034259 A1 | 3/2002 | Tada | | WO | WO-99/18870 | 4/1999 |
| 2002/0035374 A1 | 3/2002 | Borillo et al. | | WO | WO-99/18871 | 4/1999 |
| 2002/0043307 A1 | 4/2002 | Ishida et al. ................ 148/411 | | WO | WO-99/30640 | 6/1999 |
| 2002/0052572 A1 | 5/2002 | Franco et al. | | WO | WO 00/27292 | 5/2000 |
| 2002/0058989 A1 | 5/2002 | Chen et al. | | WO | WO 00/44428 | 8/2000 |
| 2002/0077555 A1 | 6/2002 | Schwartz | | WO | WO-01/21247 | 3/2001 |
| 2002/0095174 A1 | 7/2002 | Tsugita et al. | | WO | WO-01/30268 | 5/2001 |
| 2002/0096183 A1 | 7/2002 | Stevens et al. | | WO | WO 01/49185 | 7/2001 |
| 2002/0099389 A1 | 7/2002 | Michler et al. .............. 606/139 | | WO | WO-01/78596 | 10/2001 |
| 2002/0107531 A1 | 8/2002 | Schreck et al. | | WO | WO-02/17809 | 3/2002 |
| 2002/0111537 A1 | 8/2002 | Taylor et al. | | WO | WO 02/24106 | 3/2002 |
| 2002/0111637 A1 | 8/2002 | Kaplan et al. | | WO | WO-03/024337 | 3/2003 |
| 2002/0111647 A1 | 8/2002 | Khairkhahan et al. | | WO | WO-03/053493 | 7/2003 |
| 2002/0120323 A1 | 8/2002 | Thompson et al. | | WO | WO-03/059152 | 7/2003 |

| | | |
|---|---|---|
| WO | WO-03/063732 | 8/2003 |
| WO | WO 03/077733 | 9/2003 |
| WO | WO-03/082076 | 10/2003 |
| WO | WO-03/103476 | 12/2003 |
| WO | WO-2004/032993 | 4/2004 |
| WO | WO-2004/037333 | 5/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

SMST-2000, "Proceedings of the International Conference on Shape Memory and Superelastic Technologies," Apr. 30 to May 4, 2000, Asilomar Conference Center.
Ruis et al. "The Puncture Technique: A New Method for Transcatheter Closure of Patent Foramen Ovale," Cathterization and Cardiovascular Interventions 53, Wiley-Liss, Inc., 2001, pp. 369-372.
International Search Report, International Application No. PCT/US03/17390, mailed on Oct. 6, 2003, 4 pgs.
Nat'l Aeronautics and Space Administration, "55-Nitinol—The Alloy with a Memory: Its Physical Metallurgy, Properties, and Applications," A Report, pp. 24-25.
Kimura, A., et al., "Effects of Neutron Irradiation on the Transformation Behavior in Ti-Ni Alloys," Abstract, Proceedings of the Int'l Conf. On Mariensitic Transformations (1992) pp. 935-940.
Ramanathan, G., et al., "Experimental and Computational Methods for Shape Memory Alloys," 15$^{th}$ ASCE Engineering Mechanics Conf., Jun. 2-5, 2003.
Shabalovskaya, S., "Surface, corrosion and biocompatibility aspects of Nitinol as an implant material," Bio-Medical materials and Engineering, (2002) vol. 12, pp. 69-109.
Uchil, J. "Shape Memory Alloys—Characterization Techniques," Pramana—Journal of Physics, (2002) vol. 58, Nos. 5 & 6, pp. 1131-1139.
Athanasion, T., "Coronary Artery Bypass with the Use of a Magnetic Distal Anastomotic Device: Surgical Technique and Preliminary Experience," The Heart Surgery Forum #2004-1024, 2004, 4 pgs.
Bachthaler, M. et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.
European Examination Report, European Application No. 04781644.2, mailed Aug. 23, 2007 (3 Pages).
Falk, V., "Facilitated Endoscopic Beating Heart Coronary Artery Bypass Grafting Using a Magentic Coupling Device," Journal of Thoracic and Cardiovascular Surgery, vol. 126,(5), pp. 1575-1579.
Filsoufi, F., et al., "Automated Distal Coronary Bypass with a Novel Magnetic Coupler (MVP system)," J. Thoracic and Cardiovascular Surgery, vol. 127(1), pp. 185-192.
International Search Report for International Patent Application No. PCT/AU03/00759, filed Jun. 19, 2003.
International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/17715, mailed Mar. 24, 2004 (2 pgs).
International Search Report, International Application No. PCT/US03/32133, mailed Apr. 22, 2004 (1 pg).
International Search Report, International Application No. PCT/US03/34003 mailed Oct. 3, 2004 (4 pgs).
International Search Report, International Application No. PCT/US03/35479, mailed Apr. 14, 2004 (2 pgs).
International Search Report, International Application No. PCT/US03/35998 mailed Jun. 16, 2004 (5 pgs).
International Search Report, International Application No. PCT/US03/39253, mailed Apr. 19, 2004 (4 pgs).
International Search Report, International Application No. PCT/US04/022643, mailed Mar. 31, 2005 (2 pgs).
International Search Report, International Application No. PCT/US04/026998, mailed Apr. 22, 2005 (5 pgs).
International Search Report, International Application No. PCT/US04/029978, mailed Jan. 26, 2005 (3 pgs).
International Search Report, International Application No. PCT/US05/006703, mailed Jul. 25, 2005 (3 pgs).
International Search Report, International Application No. PCT/US05/013705 mailed Aug. 4, 2005 (4 pgs).
International Search Report, International Application No. PCT/US05/015382, mailed Oct. 6, 2005 (4 pgs).
International Search Report, International Application No. PCT/US05/34276, mailed Oct. 9, 2007.
International Search Report, International Application No. PCT/US06/009978, mailed Jul. 13, 2006 (2 pgs).
International Search Report, International Application No. PCT/US2007/065526, mailed Aug. 8, 2007 (5 pgs).
International Search Report, International Application No. PCT/US2007/065541, mailed Aug. 7, 2007 (3 pgs).
International Search Report, International Application No. PCT/US97/14822, mailed Feb. 20, 1998 (2 pgs).
International Search Report, International Application No. PCT/US97/17927, mailed Feb. 10, 1998 (1 pg).
Isotalo, T. et al., "Biocompatibility Testing of a New Bioabsorbable X-Ray Positive SR-PLA 96/4 Urethral Stent", *The Journal of Urology*, vol. 163, pp. 1764-1767, Nov. 1999.
Klima, U., "Magnetic Vascular Port in Minimally Invasive Direct Coronary Artery Bypass Grafting," Circulation, 2004, II-55-II-60.
Meier, MD, Bernhard et al., "Contemporary Management of Patent Foramen Ovale," American Heart Association, Inc., Circulation, 2003, vol. 107, pp. 5-9.
Parviainen, M. et al., "A New Biodegradable Stent for the Pancreaticojejunal Anastomosis After Pancreaticoduodenal Resection: In Vitro Examination and Pilot Experiences in Humans", *Pancreas*, vol. 21, No. 1, pp. 14-21, 2000.
Ruddy, A.C. et al., "Rheological, Mechanical and Thermal Behaviour of Radipaque Filled Polymers", *Polymer Processing Research Centre, School of Chemical Engineering, Queen's University of Belfast*, 5 pages.
Vaajanen, A. et al., "Expansion and Fixation Properties of a New Braided Biodegradable Urethral Stent: An Experimental Study in the Rabbit", *The Journal of Urology*, vol. 169, pp. 1771-1174, Mar. 2003.

\* cited by examiner

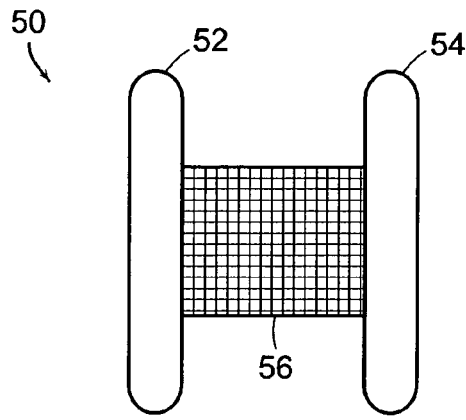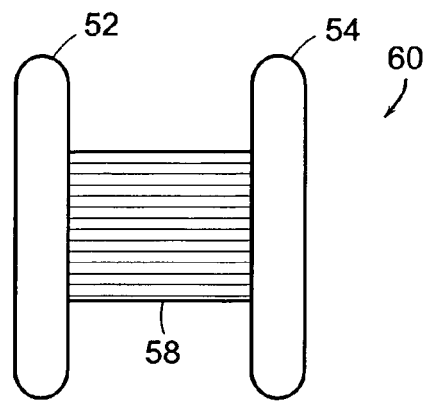
FIG. 6A　　　　　　　　FIG. 7A
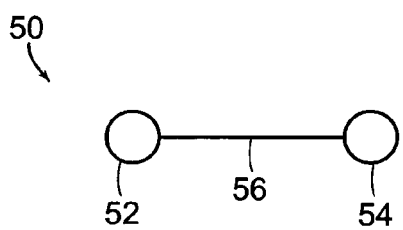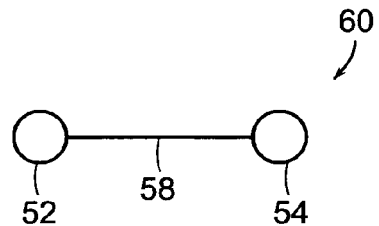
FIG. 6B　　　　　　　　FIG. 7B
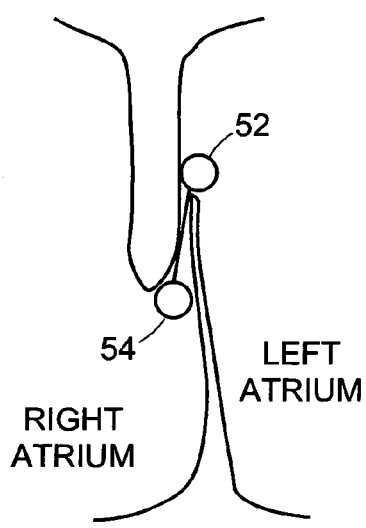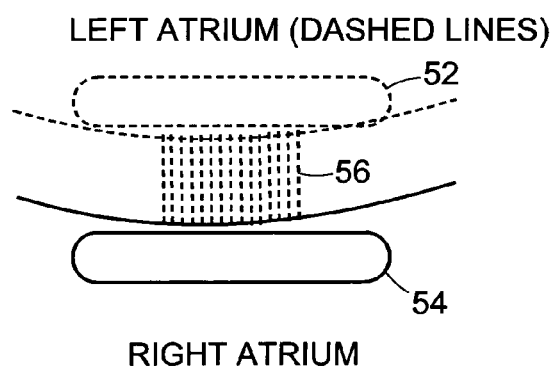
FIG. 8A　　　　　　　　FIG. 8B

SEPTAL OCCLUDER AND ASSOCIATED METHODS

RELATED APPLICATION

The present application is based on and claims priority from U.S. Provisional Patent Application Serial No. 60/340,858 filed on Dec. 19, 2001 and entitled PATENT FORAMEN OVALE (PFO) CLOSURE DEVICE WITH BIORESORBABLE COMPONENTS.

BACKGROUND OF THE INVENTION

A patent foramen ovale (PFO) as shown in FIG. 1 is a persistent, one-way, usually flap-like opening in the wall between the right atrium 10 and left atrium 12 of the heart. Since left atrial (LA) pressure is normally higher than right atrial (RA) pressure, the flap typically stays closed. Under certain conditions, however, RA pressure can exceed LA pressure creating the possibility for right to left shunting that can allow blood clots to enter the systemic circulation. In utero, the foramen ovale serves as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a probe-patent foramen ovale has been shown to persist in up to 35% of adults in an autopsy series. Using contrast echocardiography (TEE), a PFO can be detected in approximately 25% of adults. These numbers are different because an autopsy allows direct visual inspection of the anatomy, whereas contrast echocardiography relies on the measurement of an indirect physiologic phenomenon.

The cause of ischemic stroke remains cryptogenic (of unknown origin) in approximately 40% of cases. Especially in young patients, paradoxical embolism via a PFO is considered in the diagnosis. While there is currently no proof for a cause-effect relationship, many studies have confirmed a strong association between the presence of a PFO and the risk for paradoxical embolism or stroke. In addition, there is good evidence that patients with PFO and paradoxical embolism are at increased risk for future, recurrent cerebrovascular events.

The presence of PFO has no therapeutic consequence in otherwise healthy adults. In contrast, patients suffering a stroke or TIA in the presence of a PFO and without another cause of ischemic stroke are considered for prophylactic medical therapy to reduce the risk of a recurrent embolic event. These patients are commonly treated with oral anticoagulants, which have the potential for adverse side effects such as hemorrhaging, hematoma, and interactions with a variety of other drugs. In certain cases, such as when anticoagulation is contraindicated, surgery may be used to close a PFO. To suture a PFO closed requires attachment of septum secundum to septum primum with a continuous stitch, which is the common way a surgeon shuts the PFO under direct visualization.

Non-surgical closure of PFOs has become possible with the advent of umbrella-like devices and a variety of other similar mechanical closure designs developed initially for percutaneous closure of atrial septal defects (ASD). These devices allow patients to avoid the potential side effects often associated with anticoagulation therapies.

BRIEF SUMMARY OF EMBODIMENTS OF THE INVENTION

Various embodiments of the present invention are directed to devices for closing septal defects such as PFOs. The closure devices generally include a proximal anchor member, a distal anchor member, and a flexible center joint connecting the two anchor members. The center joint can be a suture. Alternatively, the center joint can be a flexible elastomeric layer, which can, e.g., be used to promote tissue ingrowth or for drug delivery. The flexible material can also be covered with a biocompatible glue to promote adherence to tissue or growth factors to accelerate tissue ingrowth.

In accordance with some embodiments of the invention, the closure device is formed of bioresorbable components such that substantially no permanent foreign body remains in the defect.

In accordance with further embodiments of the invention, mechanisms are provided to collapse the closure device for facilitating device delivery, removal and/or repositioning.

These and other features will become readily apparent from the following detailed description wherein embodiments of the invention are shown and described by way of illustration. As will be realized, the invention is capable of other and different embodiments and its several details may be capable of modifications in various respects, all without departing from the invention. Accordingly, the drawings and description are to be regarded as illustrative in nature and not in a restrictive or limiting sense.

BRIEF DESCRIPTION OF THE DRAWINGS

FIGS. 6A and 6B are front and side views, respectively, of a PFO closure device in accordance with one or more further embodiments of the invention;

FIGS. 7A and 7B are front and side views, respectively, of a PFO closure device in accordance with one or more further embodiments of the invention;

FIGS. 8A and 8B are side and front views, respectively, of the PFO closure device of FIG. 6 deployed to close a PFO;

DETAILED DESCRIPTION OF EMBODIMENTS

Various embodiments of the present invention are directed to methods and devices for closing septal defects such as PFOs, primarily by eliciting a healing response at the defect.

Figure 1:
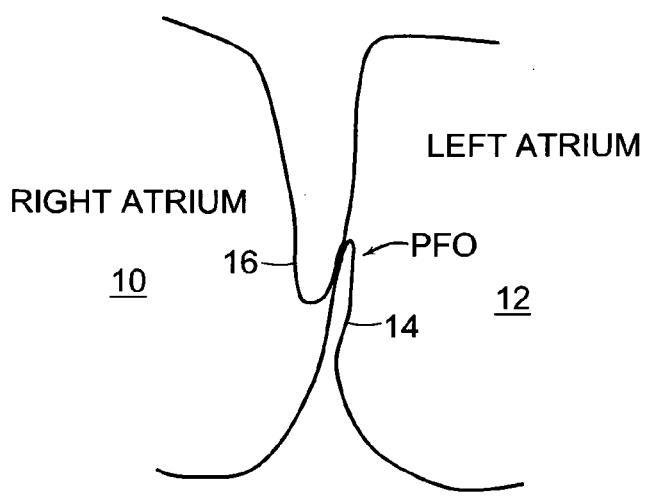
FIG. 1 is a cross-sectional view of a portion of the heart illustrating a PFO.
Figure 2:
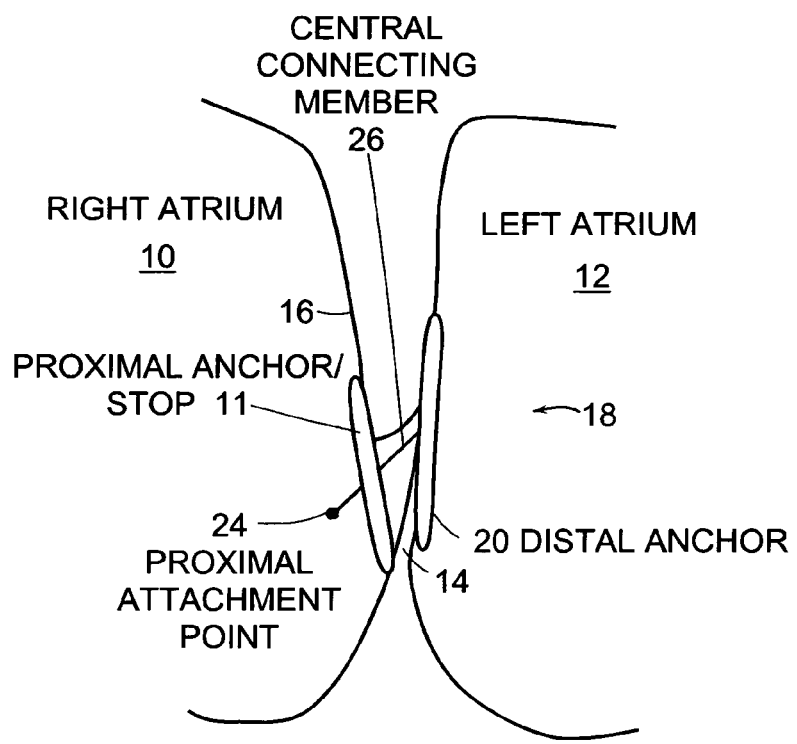
FIG. 2 illustrates a deployed PFO closure device with bioresorbable components in accordance with one or more embodiments of the invention.

As shown in FIG. 2, a PFO closure device 18 in accordance with one or more embodiments of the present invention includes a distal anchor component or member 20 (which can be placed on the left atrial side of the PFO), a proximal anchor member 22 (to fix the device in place), a proximal attachment point 24 (for attachment and release from a catheter), and a central connecting member 26 (which can, e.g., be a simple suture in accordance with this embodiment).

In some embodiments, the distal anchor, the proximal anchor, and the connecting member are bioresorbable. These components can be fabricated from either a single bioresorbable polymer or by a laminated composite of two or more materials to provide a unique mix of properties such as, e.g., anchor members having stiff centers and flexible edges, and blood contacting surfaces having controlled porosity or surface texture to promote fast and thorough endothelialization, while minimizing thrombosis. In addition, the tissue contacting surface of the anchors can be designed to provide added stability by, e.g., being roughened.

The distal anchor 20 is an elongated, preferably generally cylindrical, thin bar-like member with rounded, arcuately shaped ends. The tissue contacting surface of the anchor can be generally flattened to increase tissue surface contact. In size, the distal anchor component might, e.g., be 15-30 mm long and 2 mm in diameter with a circular cross-section. The proximal anchor 22 can be of similar dimensions and shape, although it can be shorter in overall length.

Other distal and proximal anchor structures are also possible. For example, the anchors can be formed of a generally flat material rolled to form a cylindrical shape as described below with respect to the embodiments of FIGS. 20 and 21.

Figure 3:
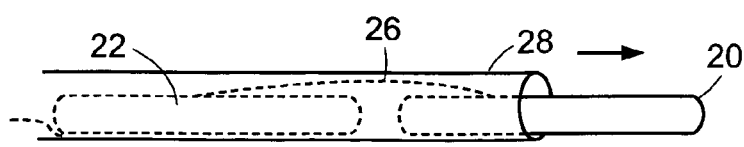
FIG. 3 illustrates the PFO closure device of FIG. 2 in a collapsed state for passage through a delivery catheter or sheath.

For delivery and deployment, the distal anchor 20 and proximal anchor 22 are positioned to be generally aligned in a longitudinal, end-to-end manner within a delivery sheath or catheter 28 as shown in FIG. 3. These components, with the flexible connecting member 26 traverse the catheter or delivery sheath in this longitudinal orientation. The catheter or delivery sheath is inserted between septum primum and septum secundum into the left atrium 18, and the distal anchor component 20 is ejected. Then, the catheter or delivery sheath 28 is withdrawn into the right atrium, and the proximal anchor 22 is ejected. The flexible central connecting member 26 extends between septum primum and septum secundum to join the distal anchor 20 and the proximal anchor 22. Once ejected, the distal anchor and proximal anchor generally self-orientate to be essentially perpendicular to the axis of the central connecting member and in generally parallel planes to one another. The exact orientation will be governed by the individual patient anatomy.

An alternate delivery method for this device can be to deploy it directly through the septum primum as opposed to through the PFO.

The method of attaching the central connecting member 26 to the anchor and stop mechanism 22 to permit the distal anchor and the proximal anchor to be drawn together could be, e.g., via a friction fit or via a slip knot on the central connecting member. If a slip knot is used, the free end of the suture proximal to the knot can be held remotely and released after the knot has been placed in the appropriate location.

Figure 4:
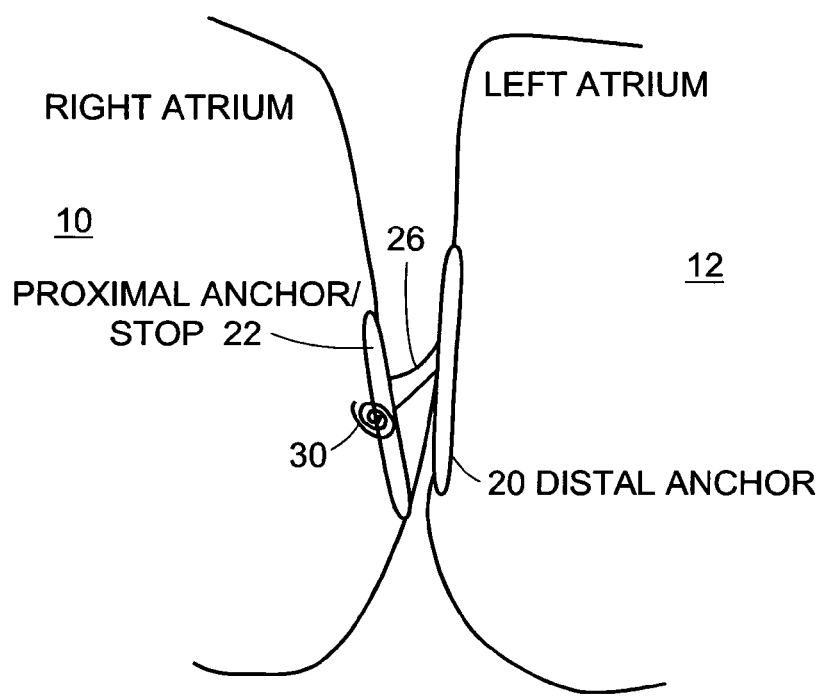
FIG. 4 illustrates a closure device deployed to close a PFO in accordance with one or more further embodiments of the invention.

In one or more alternate embodiments of the invention shown in FIG. 4, the central connecting member 26 is mounted to permit free sliding movement of the proximal anchor 22 relative to the central connecting member 26. A biasing spring 30, which may be an expandable coil spring, can be formed at the outer end of the central connecting member 26 to bias the proximal anchor toward the distal anchor when both are deployed from the catheter or sheath.

Figure 5:
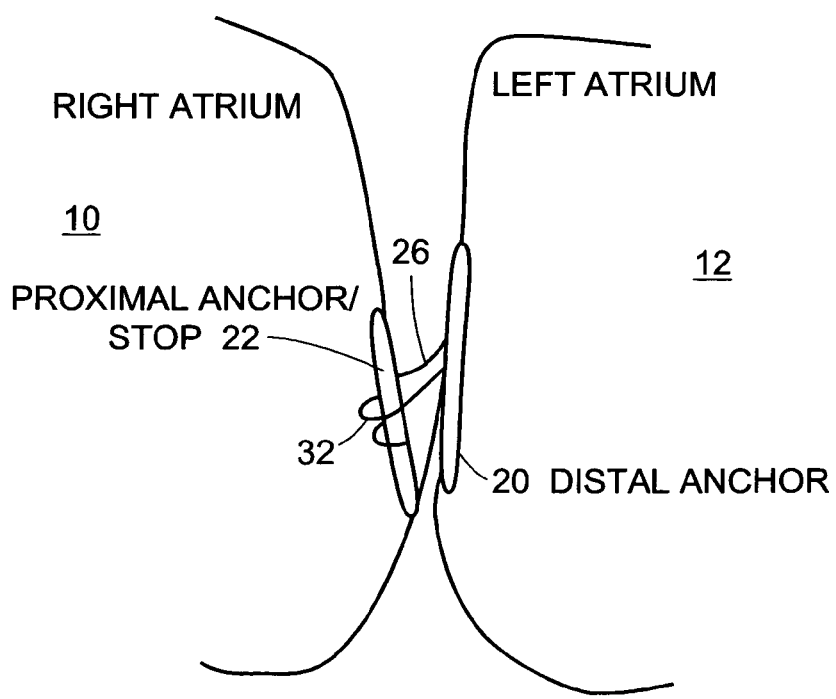
FIG. 5 illustrates a closure device deployed to close the PFO in accordance with one or more further embodiments of the invention.

In the embodiments illustrated in FIGS. 4 and 5, a metallic component may be used as the central connecting member 26 in order to provide an appropriate stop and apply compression force to the proximal anchor 22. The metallic component could be a piece of shape memory wire that has one end molded or laminated into the distal anchor component 20. In FIG. 4, the proximal anchor 22 slides on the central connecting member 26, and once it is deployed, the biasing spring 30 formed on the end of the shape memory wire expands to bias the proximal anchor 22 toward the distal anchor 20.

In the FIG. 5 embodiment, a shape memory wire forms a hook type anchor 32 made from two wires that exit through the center of the proximate anchor and curve in opposite directions when expanded to draw the proximate anchor toward the distal anchor.

While the embodiments of FIGS. 4 and 5 can leave a permanent foreign body when the bioresorbable components dissolve (if, e.g., a metallic component is used as the central connecting member 26), one advantage of these devices is that no thrombogenic tissue scaffold (usually a vascular material) is placed on the left atrial side. Thrombus forming on the LA side of a PFO closure device can be released into the systemic circulation causing an embolic event within the coronary arteries, cerebral circulation, or distally in the vasculature, and most vascular graft materials utilized to close PFOs are highly thrombogenic.

The PFO closure devices may need to be capable of x-ray visualization and use with radiopaque fillers or marker bands fabricated from noble metals such as platinum or gold. These markers can be attached using a variety of common methods such as, e.g., adhesive bonding, lamination between two layers of polymer, or vapor deposition.

FIGS. 6A and 6B illustrate a closure device 50 in accordance with one or more further embodiments of the invention. The device 50 includes proximal and distal anchor members 52, 54 connected with a flexible (and preferably stretchable elastomeric) center joint or connecting element 56. The anchor members 52, 54 are preferably cylindrical in shape with rounded ends. In size, the distal anchor member 54 might, e.g., be about 15-30 mm long and about 2 mm in diameter with a circular cross-section. The proximal anchor 52 can be of similar dimensions and shape, although it can be shorter in overall length. The anchor members 52, 54 are preferably made from a rigid (preferably bioresorbable) polymer (regular or shape memory), or biological tissue. Biocompatible metal can also be used.

Other distal and proximal anchor structures are also possible. For example, the anchors can be formed of a generally flat material rolled to form a cylindrical shape as described below with respect to the embodiments of FIGS. 20 and 21.

The center joint 56 of the FIG. 6 device (as well as the center joints of the devices shown in FIGS. 7-10, 12-18, and 21-24) are preferably elastomeric and resilient and are made from thrombogenic or inflammatory materials including, e.g., polyester, biological tissue, bioresorbable polymer, small diameter springs (e.g., Nitinol), or spongy polymeric material. Alternatively, the center joint can be made of multiple strands of material 58 such as, e.g., polymer fibers as shown in the closure device 60 of FIGS. 7A and 7B. The center joint can be textured, porous or in a form of a single or double-sided hook material such as Velcro. These kinds of surfaces produce inflammatory responses and therefore, promote faster tissue ingrowth and faster defect closure. The entire device or parts of it can be made from bioresorbable polymers.

FIGS. 8A and 8B are front and side views, respectively, of the device 50 in a PFO defect. The proximal and distal anchor members 54, 52 are longer than the defect width, thereby inhibiting the device from being embolized.

Figure 9A:
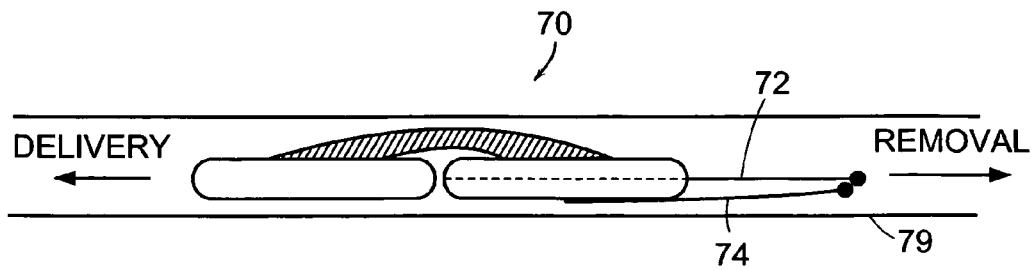
FIG. 9A illustrates a closure device having a retrieval mechanism in accordance with one or more further embodiments of the invention in a collapsed state for passage through a catheter or sheath.
Figure 9B:
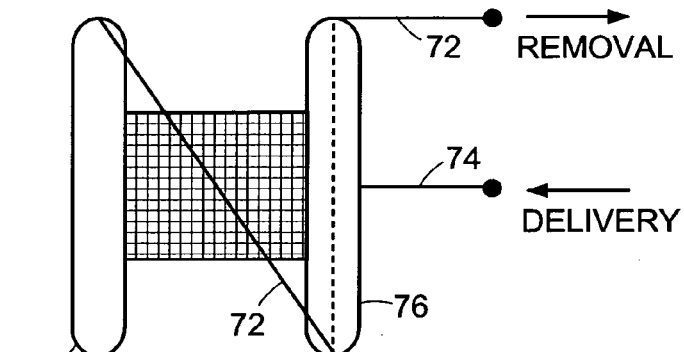
FIG. 9B is a front view of the FIG. 9A device.

In accordance with further embodiments of the invention, a closure device can include a delivery/removal mechanism to facilitate device delivery, removal or repositioning. A device 70 shown in FIGS. 9A and 9B includes a removal string 72 and a delivery string 74. The removal string is movably secured and slides freely inside of the proximal anchor member 76. The string extends from one end of the proximal member 76 and is fixed to an opposite end of the distal anchor member 78. By pulling on the free end of the removal string 72, the whole device 70 can be collapsed and pulled into the delivery sheath 79 as shown in FIG. 9A. The strings can, e.g., be sutures or wires such as Nitinol wire.

Figure 9C:
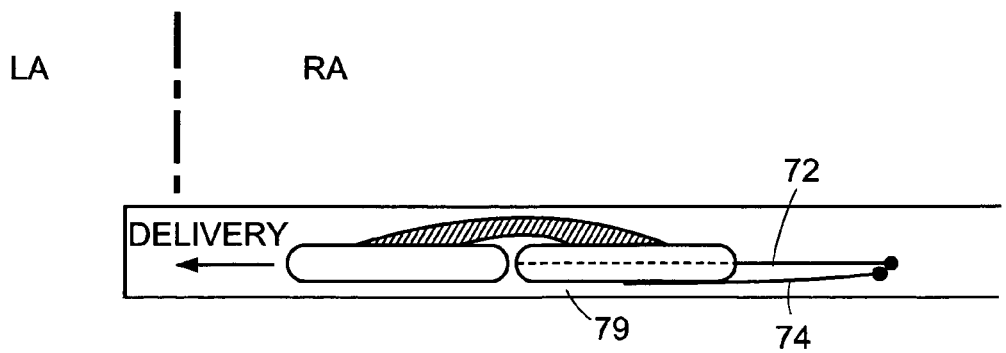
FIGS. 9C-E illustrate deployment of the FIG. 9A device.
Figure 9D:
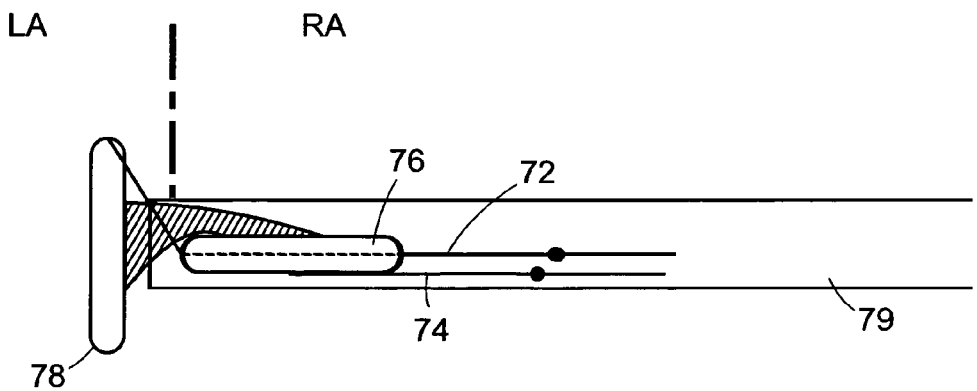
Figure 9E:
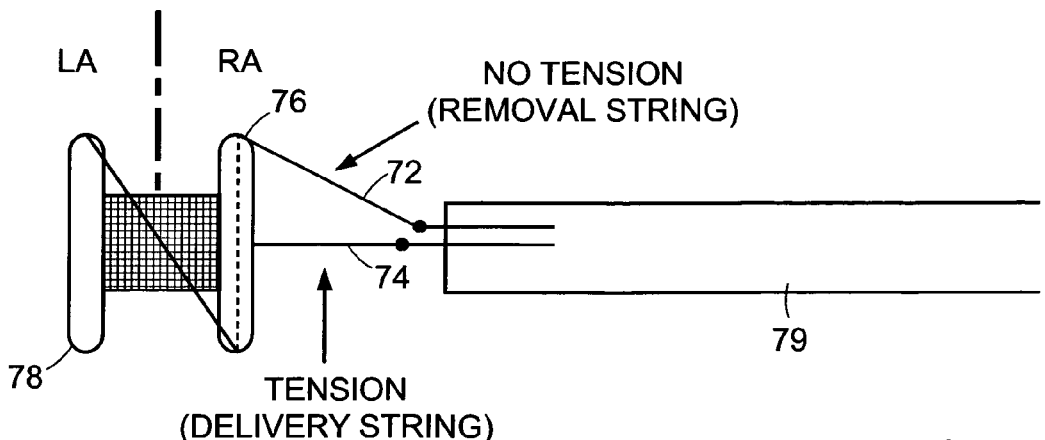

The delivery and removal strings are manipulated separately in order to deploy or remove the device. FIGS. 9C-E illustrate device deployment using the delivery string 74, which is preferably attached generally to the center of the proximal anchor member 76. The delivery sheath 79 containing the device 70 is first inserted between the septum primum and septum secundum into the left atrium as shown in FIG. 9C. As shown in FIG. 9D, the distal anchor 78 is then ejected from the delivery catheter 79. Tension is then applied to the delivery string 74, and the delivery sheath is withdrawn into the right atrium and the proximal anchor 76 is ejected. Applying tension to the delivery string enables the proximal anchor 76 to be properly deployed in the right atrium, and keeps the anchor 76 from being ejected into the left atrium. Upon successful deployment of the device 70, both strings are released and the delivery system is withdrawn. No tension is applied to the removal string during delivery.

Figure 9F:
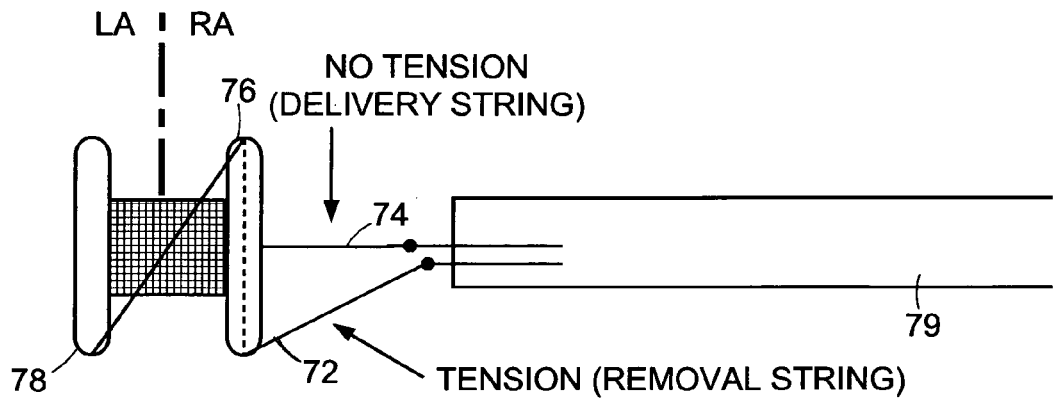
FIGS. 9F-H illustrate removal of the FIG. 9A device.
Figure 9G:
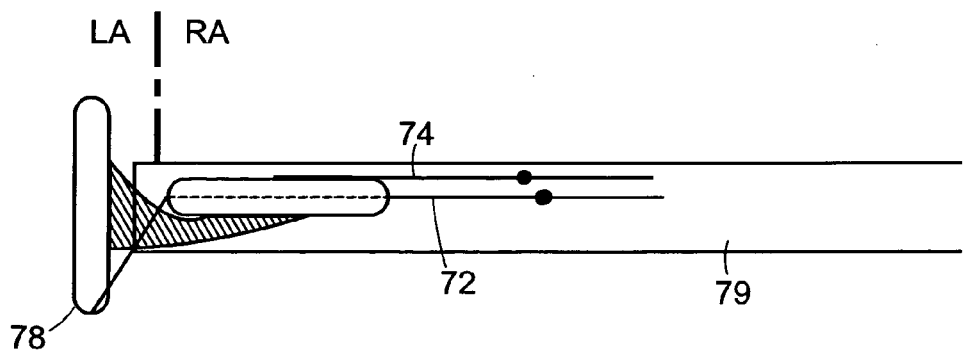
Figure 9H:
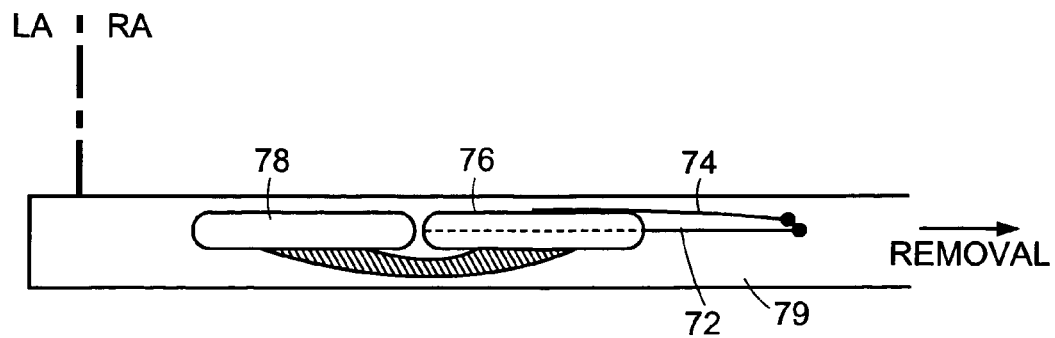

FIGS. 9F-H illustrate removal of the device 70. As shown in FIG. 9F, tension is applied to the removal string, while the delivery sheath 79 is moved toward the device 70. The applied tension causes the proximal anchor 76 to be withdrawn into the delivery sheath as shown in FIG. 9G. The distal anchor 78 is also withdrawn into the delivery sheath as further tension is applied to the removal string. The device can then be redeployed if desired or removed.

Alternatively, the delivery string 74 can be omitted, and the removal string 72 be used for both device deployment and removal. The delivery sheath 79 containing the closure device is first inserted between the septum primum and septum secundum into the left atrium in a similar manner to that shown in FIG. 9C. The distal anchor 78 is then ejected from the delivery catheter 79 in a similar manner to that shown in FIG. 9D. Tension is applied to the removal string 72, and the delivery sheath is withdrawn into the right atrium, and the proximal anchor 76 is ejected. Applying tension to the removal string enables the proximal anchor 76 to be properly deployed in the right atrium, and keeps the proximal anchor 76 from being ejected into the left atrium. The elasticity of the center joint connecting the anchor members helps properly position the proximal anchor at the defect. Upon successful deployment of the closure device, the string 72 is released and the delivery system is withdrawn.

Figure 10A:
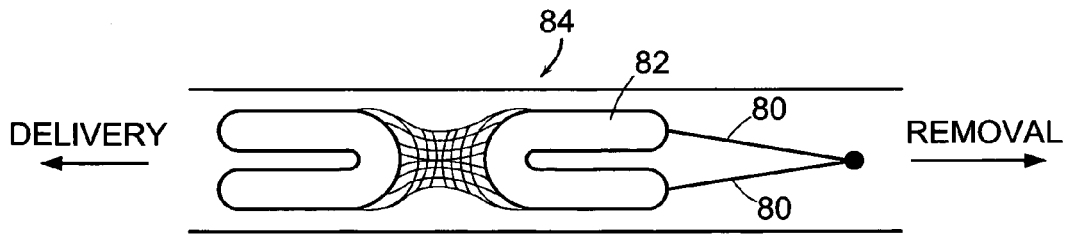
FIG. 10A illustrates a closure device having a retrieval mechanism in accordance with one or more further embodiments of the invention in a collapsed state for passage through a catheter or sheath.
Figure 10B:
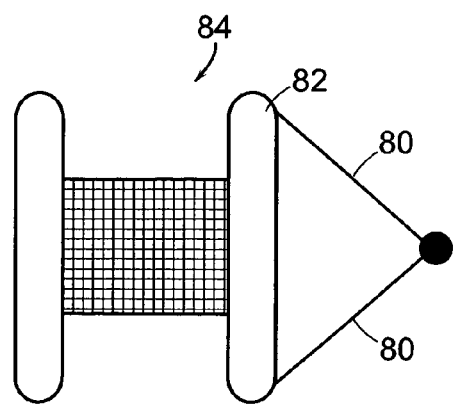
FIG. 10B is a front view of the FIG. 10A device.

As shown in FIGS. 10A and 10B, in another embodiment, strings 80 (suture, Nitinol wire, etc.) are attached to both ends of the proximal anchor member 82 of a closure device 84. Both anchor members are flexible and can fold as shown in FIG. 10A in order to be delivered to or removed from the defect.

Figure 11A:
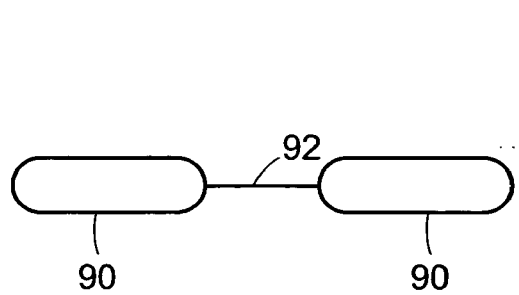
FIGS. 11A and 11B illustrate an anchor member with an elastic hinge in accordance with one or more further embodiments of the invention.
Figure 11B:
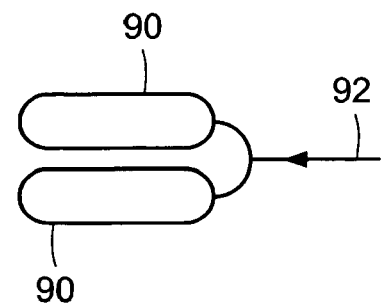

In accordance with a further embodiment of the invention, as shown in FIGS. 11A and 11B, each of the proximal and distal anchor members can include two elements 90 separated by an elastic hinge 92. The elastic hinge 92 can facilitate folding of the members as shown in FIG. 11B. The hinge 92 can be molded or made from a material such as, e.g., Nitinol or other shape memory materials, which can be a different material from the elements 90.

Figure 12:
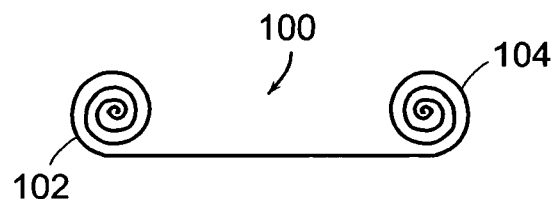
FIG. 12 illustrates a PFO closure device made from a single material in accordance with one or more further embodiments of the invention.

In accordance with some embodiments of the invention, an entire closure device can be made from a single sheet of a material as shown, e.g., in the closure device 100 of FIG. 12.

Two opposite ends of the sheet can be rolled to form the proximal and distal anchor members. Glue or heat bonding can be used to maintain the rolled-up configuration of the anchor members 102, 104.

Figure 13:
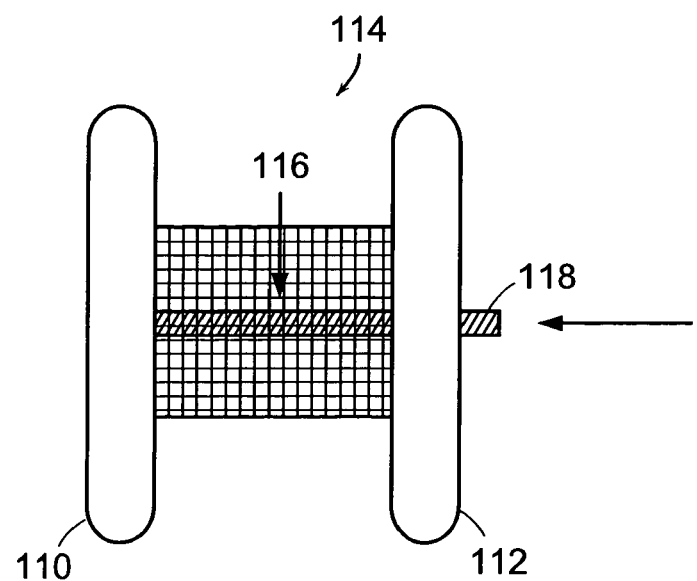
FIG. 13 illustrates a PFO closure device having inflatable anchor members in accordance with one or more further embodiments of the invention.

As shown in FIG. 13, in accordance with some further embodiments of the invention, one or both anchor members 110, 112 of a closure device 114 can be inflatable. The anchor members can be inflated with, e.g., saline or other physiological fluid during or before the delivery of the device. A tube 116 can communicate with cavities in the anchor members. An inlet 118 can be provided at one of the members for introducing fluid therein.

Figure 14:
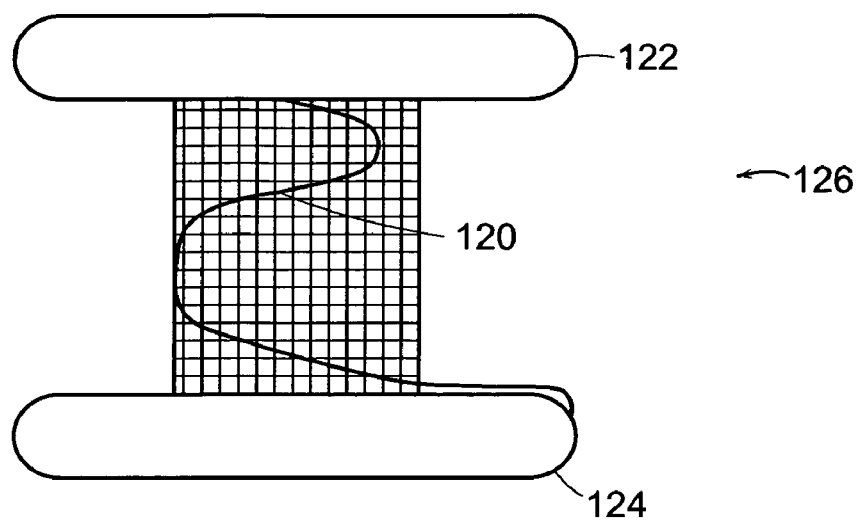
FIG. 14 illustrates a PFO closure device with a wire connecting the proximal and distal anchor members in accordance with one or more further embodiments of the invention.

In accordance with some further embodiments of the invention, a wire 120 such as, e.g., an S-shaped wire, can be provided to connect the proximal and distal anchor members 122, 124 of a device 126 as shown in FIG. 14. The wire can be used to provide additional clamping force while the device is in a PFO defect. Other wire shapes are also possible.

Figure 15:
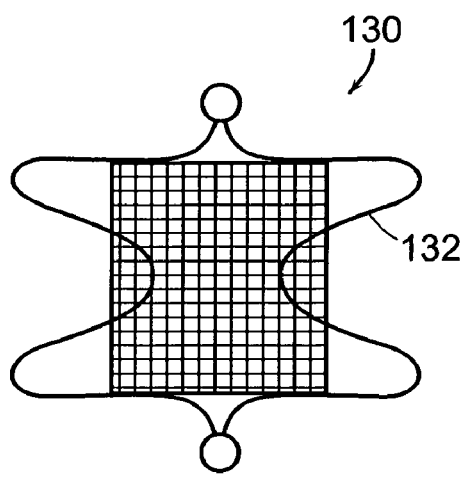
FIG. 15 illustrates a PFO closure device having a frame member in accordance with one or more further embodiments of the invention.
Figure 16:
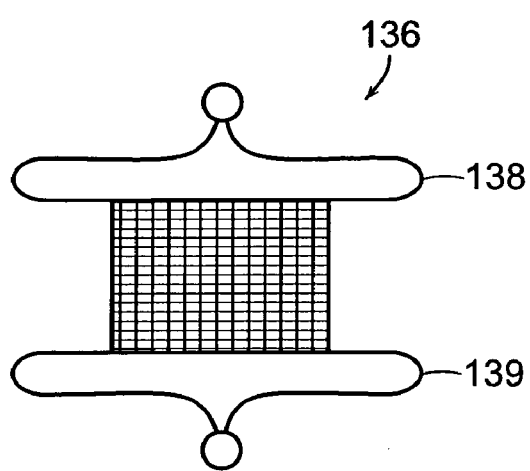
FIG. 16 illustrates a PFO closure device having frame anchor members in accordance with one or more further embodiments of the invention.

In accordance with further embodiments of the invention, one or more frame structures can be used as the anchor members of a closure device. For example, FIG. 15 shows a closure device 130 having a frame structure 132. Also, FIG. 16 shows a closure device 136 having frames 138, 139. The frames can be, e.g., a metal (e.g., Nitinol wire) or polymer frame.

Figure 17:
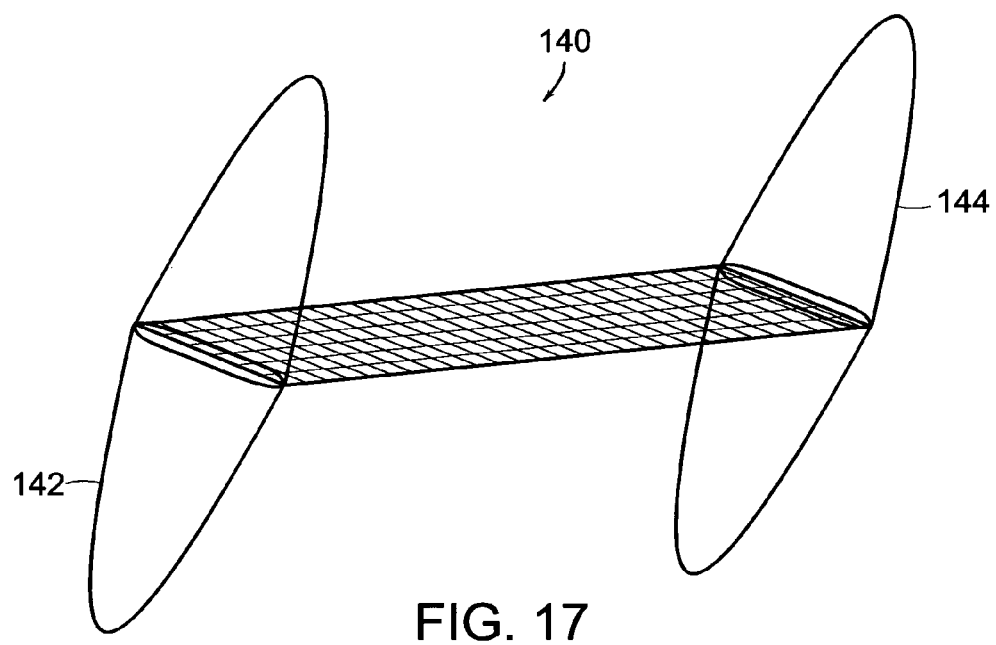
FIG. 17 illustrates a PFO closure device having frame anchor members in accordance with one or more further embodiments of the invention.
Figure 18:
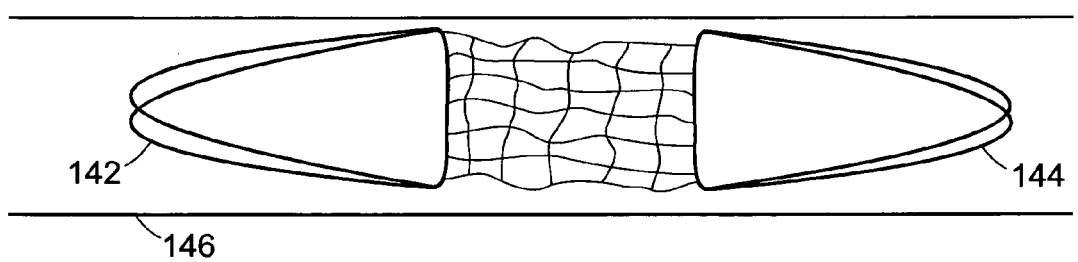
FIG. 18 illustrates the FIG. 17 device in a collapsed state for passage through a catheter or sheath.
Figure 19:
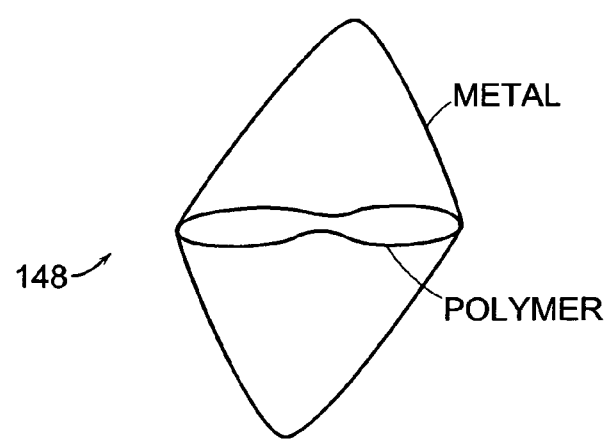
FIG. 19 illustrates a frame anchor member having metal and polymer components in accordance with one or more further embodiments of the invention.

FIGS. 17-19 illustrate closure devices in accordance with some further embodiments of the invention. A closure device 140 shown in FIG. 17 includes anchor members 142, 144 having a frame structure. The frame shape can be polygonal as shown in the figure or it can alternatively be a circular shape. Other frame shapes are also possible as, e.g., will be described below with respect to FIGS. 22-24.

A recovery suture can be attached to opposite ends of the proximate anchor member 142 to collapse the anchors for delivery in a catheter 146 as shown in FIG. 18 or for retrieval or repositioning. The anchor members can be made from a metal, preferably Nitinol, or polymers. Alternatively, as shown in FIG. 19, an anchor member 148 can include both metal and polymer components.

Figure 20A:
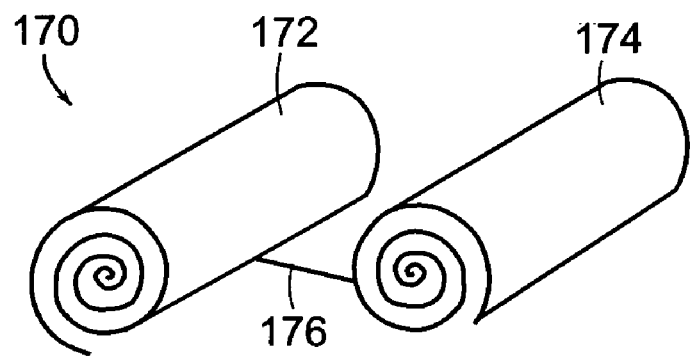
FIGS. 20A and 20B illustrate a PFO closure device having anchor members formed from a rolled material in accordance with one or more further embodiments of the invention in rolled and unrolled positions, respectively.

In accordance with one or more further embodiments of the invention, the distal and proximal anchors can be formed of a flat sheet-like member rolled to form a cylindrical shape as shown, e.g., in the device 170 of FIG. 20A. The anchors 172, 174 can unroll to form sheet-like members when deployed as shown generally in FIG. 20B. The sheet-like member can be made of a material having shape memory properties such as, e.g., shape memory polymeric materials. Alternately, the sheet-like member can include metal struts made of shape memory metals such as, e.g., Nitinol or Nitinol alloys. The shape memory materials allow the device to be delivered in a delivery sheath or catheter with the anchors in the rolled configuration of FIG. 20A. The anchors attain the sheet-like geometry of FIG. 20B once deployed due to their shape memory properties. The anchor members 172, 174 can be connected to each other with a connecting member 176, which can, e.g., be a suture similar to that used in the FIG. 2 device.

Figure 20B:
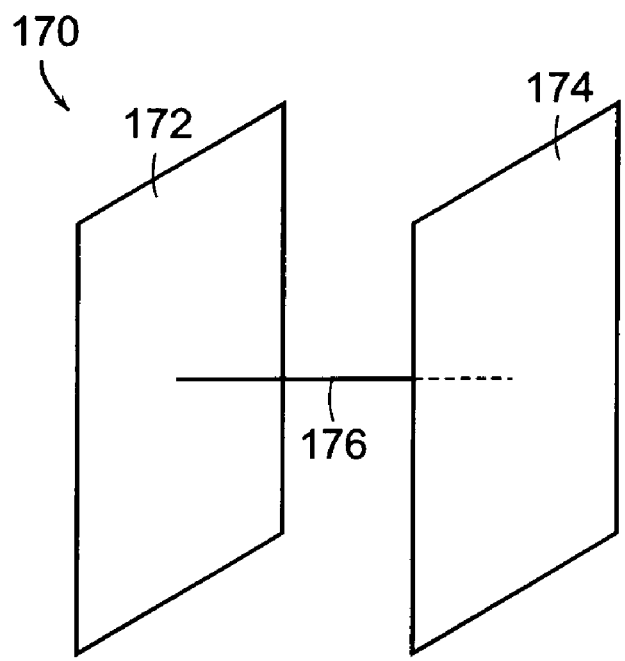
Figure 21A:
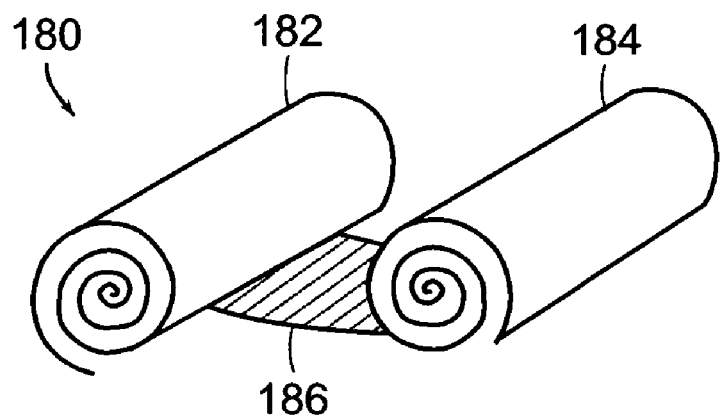
FIGS. 21A and 21B illustrate an alternate PFO closure device having anchor members formed from a rolled material in accordance with one or more further embodiments of the invention in rolled and unrolled positions, respectively.
Figure 21B:
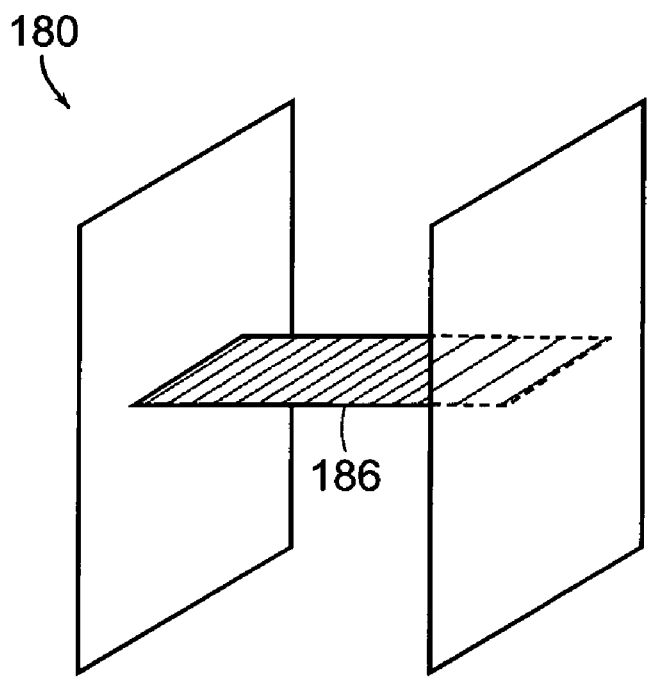

FIGS. 21A and 21B illustrate a closure device 180 having rolled anchor members 182, 184, which are similar to the anchor members 172, 174 of the device of FIGS. 20A and 20B. The anchors 182, 184 are connected to each other by a connecting member or joint 186, which can be a sheet of flexible material similar to the connecting members previously described with respect to FIGS. 6 and 7.

Figure 22A:
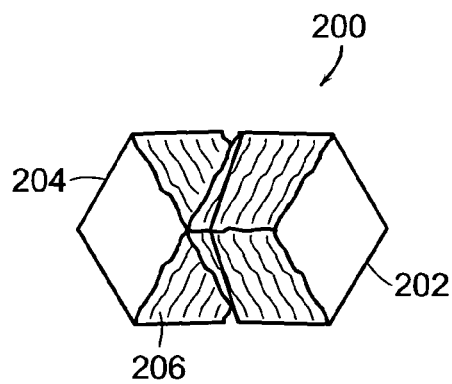
FIG. 22A illustrates a closure device having frame anchor members and a generally "X" shaped joint member in accordance with one or more further embodiments of the invention.
Figure 22B:
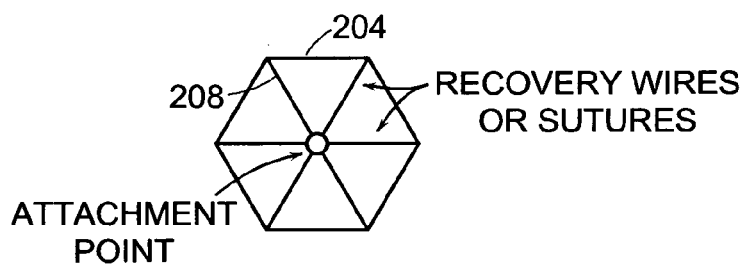
FIG. 22B illustrates the proximal anchor member of the FIG. 22A device.
Figure 22C:
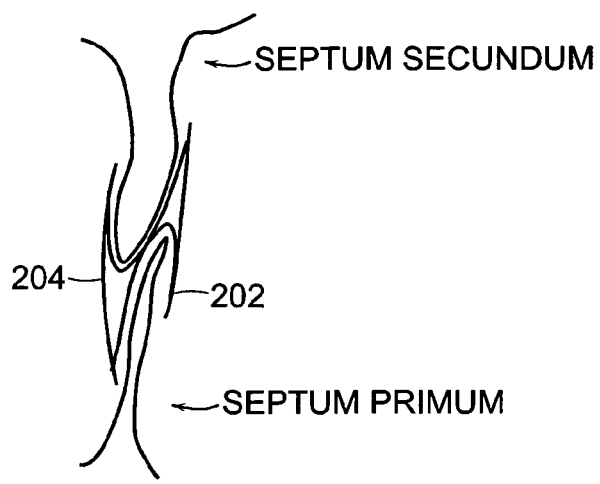
FIG. 22C illustrates the FIG. 22A device in a deployed state.

FIG. 22A illustrates a closure device 200 in accordance with one or more further embodiments of the invention. The device 200 includes distal and proximal anchor members 202, 204, each of which has a polygonal or circular frame structure. The anchor members are connected by a connecting member 206, which can be made from a flexible material similar to that previously described in connection with FIGS. 6 and 7. The connecting member 206 can be made of two sheets of flexible material connected at their centers, generally forming an "X" shape in the side view of the device. As shown in FIG. 22B, the proximal anchor member 204 can include one or more recovery wires or sutures attached to the frame structure for use in device deployment of recovery. FIG. 22C illustrates the device 200 as deployed.

Figure 23:
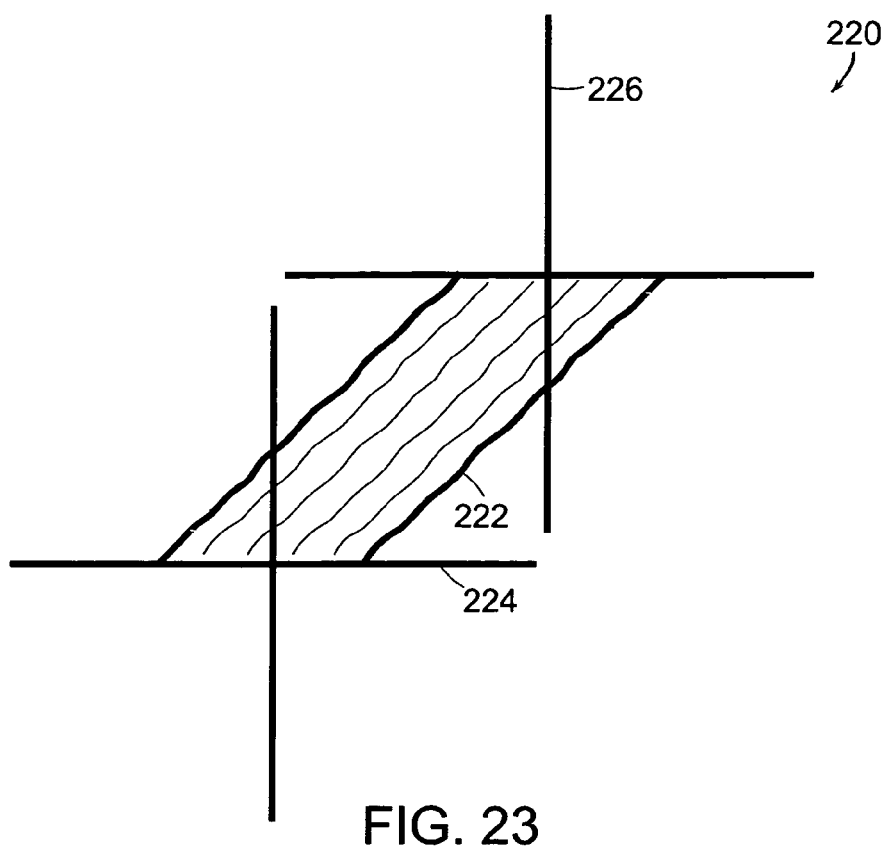
FIG. 23 illustrates a closure device having frame anchor members having a generally "+" shaped frame structure in accordance with one or more further embodiments of the invention.
Figure 24:
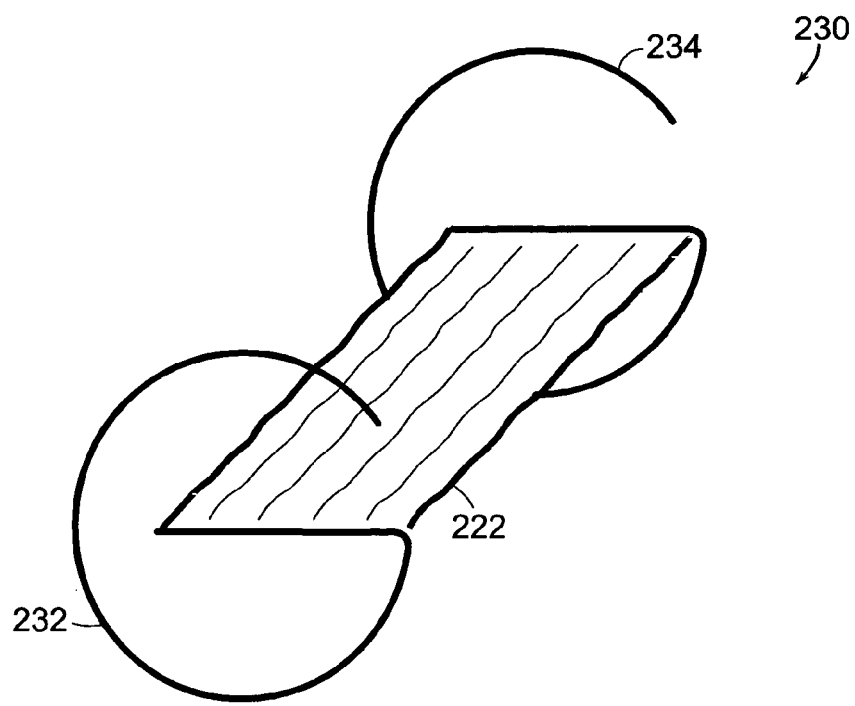
FIG. 24 illustrates a closure device having frame anchor members having a generally "G" shaped frame structure in accordance with one or more further embodiments of the invention.

FIGS. 23 and 24 illustrate closure devices 220, 230, respectively, in accordance with further embodiments of the invention. Each device 220, 230 includes distal and proximal anchor members having a frame structure. The anchor members are connected by a flexible joint 222, which can be made from a flexible material similar to that previously described in connection with FIGS. 6 and 7. The FIG. 23 device 220 includes distal and proximal anchor members 224, 226 generally having a "+" shape. The FIG. 24 device 230 includes distal and proximal anchor members 232, 234 generally having a "G" shape.

The closure devices described herein can optionally be used along with suturing or stapling techniques where the anchors or flexible joints of the devices can be sewn or stapled to septum primum or secundum for better dislodgment resistance. Also, the flexible joint can, if desired, be covered with biocompatible glue to adhere to the tissue or can be loaded with drugs or growth factors to promote healing. The glue and also certain drugs can also optionally be stored in any cavities in the anchor members (e.g., in the cylindrical members of FIGS. 6 and 7) and released after deployment. Noble metal markers can also be attached to the closure devices for a better x-ray visualization.

The various closure devices described herein can include a number of advantageous features. The closure devices preferably have an atraumatic shape to reduce trauma during deployment or removal. In addition, the devices can be self-orienting for ease of deployment. Furthermore, because of the flexible center joint, the devices generally conform to the anatomy instead of the anatomy conforming to the devices, which is especially useful in long tunnel defects. In addition, the devices can preferably be repositioned or/and removed during delivery. The devices also generally have a relatively small profile after deployment. The flexible center joint of the devices can encourage faster tissue ingrowth and therefore, faster defect closure. Furthermore, there are generally no exposed thrombogenic components on the left and right atrial sides. The devices can also advantageously include bioresorbable components, which can disappear over time.

Other benefits of the devices can include possible use of a relatively small diameter delivery sheath, use of reduced or no metal mass in the device, ease of manufacturing, cost effectiveness, and overall design simplicity.

Having described preferred embodiments of the present invention, it should be apparent that modifications can be made without departing from the spirit and scope of the invention.

The invention claimed is:

1. A septal occluder, comprising:
    a proximal generally cylindrically shaped anchor member having an axial length and an outer surface for deployment proximate a first end of a septal defect;
    a distal generally cylindrically shaped anchor member having an axial length and an outer surface for deployment proximate a second end of said septal defect; and
    a flexible connection layer, having a width and a length, fixedly attached to said proximal anchor member along a proximal attachment line and fixedly attached to said distal anchor member along a distal attachment line, the proximal attachment line extending in an axial direction on the outer surface of the proximal anchor member, the distal attachment line extending in an axial direction on the outer surface of the distal anchor member, and at least one of the distal attachment line and proximal attachment line being along the width of the flexible connection layer;

said proximal and distal anchor members and said flexible connection layer comprising one or more bioresorbable materials.

2. The septal occluder of claim 1 wherein said proximal and distal anchor members each have a first end and a second end and wherein each of the first ends and second ends are rounded.

3. The septal occluder of claim 1 wherein said proximal and distal anchor members each comprise a cylindrical structure formed by rolling a layer of material.

4. The septal occluder of claim 1 wherein said proximal and distal anchor members are inflatable.

5. The septal occluder of claim 1 wherein said septal occluder is collapsible for passage through a catheter or sheath.

6. The septal occluder of claim 5 wherein said occluder can be collapsed with the proximal and distal anchor members being in a generally aligned, end to end arrangement for passage through a catheter or sheath.

7. The septal occluder of claim 1 wherein said proximal and distal anchor members are collapsible for deployment or removal.

8. The septal occluder of claim 7 wherein the proximal and distal anchor members are generally foldable.

9. The septal occluder of claim 8 wherein each anchor member includes two elements separated by an elastic hinge.

10. The septal occluder of claim 1 further comprising a removal string attached to the septal occluder to facilitate removal of the septal occluder from the septal defect.

11. The septal occluder of claim 10 wherein said removal string is slidingly mounted in said proximal anchor member and attached to said distal anchor member.

12. The septal occluder of claim 10 wherein said removal string is mounted to slide through said proximal anchor member.

13. The septal occluder of claim 10 further comprising a delivery string to facilitate deployment of the septal occluder at the septal defect.

14. The septal occluder of claim 1 wherein said septal occluder is formed from a layer of material having opposite ends rolled to form the proximal and distal anchor members.

15. The septal occluder of claim 1 further comprising a wire connecting said proximal and distal anchor members to provide clamping force to close the defect.

16. The septal occluder of claim 15 wherein said wire has a serpentine configuration.

17. The septal occluder of claim 1 wherein said flexible connection layer comprises a layer of elastomeric material.

18. The septal occluder of claim 1 wherein said flexible connection layer comprises a layer of material made from thrombogenic or inflammatory materials.

19. The septal occluder of claim 1 wherein said flexible connection layer comprises a layer of material that is porous or textured.

20. The septal occluder of claim 1 wherein said flexible connection layer comprises a layer of material that is covered with a biocompatible glue to promote adherence to tissue.

21. The septal occluder of claim 1 wherein said flexible connection layer comprises a layer of material that is covered with growth factors to accelerate tissue ingrowth.

22. The septal occluder of claim 1, wherein at least one of said proximal and distal anchor members is configured to move pivotally relative to said flexible connection layer.

23. A septal defect closure device, comprising:
an elongated proximal anchor member, having a length along a longitudinal axis longer than its transverse dimension for deployment proximate a first end of a septal defect;
an elongated distal anchor member, having a length along a longitudinal axis longer than its transverse dimension, for deployment proximate a second end of said septal defect; and
a flexible layer having a width and a length, said flexible layer being fixedly attached to said proximal anchor member at a first connection location and fixedly attached to said distal anchor member at a second connection location, wherein at least one of the first and second connection locations forms a juncture line along the width of the flexible layer and along a portion of an axial length of the corresponding anchor member.

24. The device of claim 23 wherein said flexible layer comprises thrombogenic or inflammatory materials.

25. The device of claim 23 wherein said flexible layer is porous or textured.

26. The device of claim 23 wherein said flexible layer is covered with a biocompatible glue to promote adherence to tissue.

27. The device of claim 23 wherein said flexible layer is covered with growth factors to accelerate tissue ingrowth.

28. The device of claim 23 wherein said flexible layer comprises a resilient elastomeric material.

29. The device of claim 23 wherein said flexible layer comprises a plurality of fibers connecting the anchor members.

30. The device of claim 23 wherein said proximal and distal anchor members each have a generally cylindrical shape with rounded ends.

31. The device of claim 23 wherein a side of each anchor member for contacting a tissue surface is generally flattened to increase surface contact.

32. The device of claim 23 wherein said proximal and distal anchor members each comprise a cylindrical structure formed by rolling a layer of material.

33. The device of claim 23 wherein said proximal and distal anchor members are inflatable.

34. The device of claim 23 wherein said device is collapsible for passage through a catheter or sheath.

35. The device of claim 34 wherein said occluder can be collapsed with the proximal and distal anchor members being in a generally aligned, end to end arrangement for passage through a catheter or sheath.

36. The device of claim 23 wherein said proximal and distal anchor members are collapsible for deployment or removal.

37. The device of claim 36 wherein the proximal and distal anchor members are generally foldable.

38. The device of claim 37 wherein each anchor member includes two elements separated by an elastic hinge.

39. The device of claim 23 further comprising a removal string attached to the device to facilitate removal of the device from the septal defect.

40. The device of claim 39 wherein said removal string is slidingly mounted in said proximal anchor member and attached to said distal anchor member.

41. The device of claim 39 wherein said removal string is mounted to slide through said proximal anchor member.

42. The device of claim 39 further comprising a delivery string to facilitate deployment of the device at the septal defect.

43. The device of claim 23 wherein said device is formed from a layer of material having opposite ends rolled to form the proximal and distal anchor members.

44. The device of claim 23 further comprising a wire connecting said proximal and distal anchor members to provide clamping force to close the defect.

45. The device of claim 44 wherein said wire has a serpentine configuration.

46. A septal defect closure device, comprising:
a generally cylindrically shaped proximal anchor member for deployment proximate a first end of a septal defect, the proximal member has a length along an axial dimension that is greater than the transverse dimension and an outer surface;
a distal anchor member having an outer surface for deployment proximate a second end of said septal defect;
a flexible connection layer, having a width and a length, fixedly attached to said proximal anchor along a proximal attachment line and fixedly attached to said distal anchor member along a distal attachment line,
wherein the flexible connection layer is fixedly attached to the proximal anchor member during delivery of the device to the septal defect,
wherein the proximal attachment line extends in an axial direction on the outer surface of the proximal anchor member, the distal attachment line extends in an axial direction on the outer surface of the distal anchor member, and at least one of the distal attachment line and proximal attachment line being along the width of the flexible connection layer; and
a removal string extending from said proximal anchor member to facilitate collapsing and removal of the device from the septal defect.

47. The device of claim 46 wherein said removal string is slidingly mounted in said proximal anchor member and attached to said distal anchor member.

48. The device of claim 46 wherein said removal string is mounted to slide through said proximal anchor member.

49. The device of claim 46 further comprising a delivery string to facilitate deployment of the device at the septal defect.

50. The device of claim 46 wherein said proximal and distal anchor members are collapsible for deployment or removal.

51. The device of claim 50 wherein the proximal and distal anchor members are generally foldable.

52. The device of claim 51 wherein each anchor member includes two elements separated by an elastic hinge.

53. The device of claim 46 wherein a delivery string is attached to the proximal anchor member at a generally central location on the proximal anchor member.

54. The device of claim 46 wherein said removal string is usable for both removal and deployment of the device.

55. The device of claim 46, wherein at least one of said proximal and distal anchor members is configured to move pivotally relative to said flexible connection layer.

56. An apparatus for closing a septal defect, comprising:
a delivery system including a sheath having a tip positionable at the defect; and
a septal occluder collapsible for delivery through the sheath for deployment at the septal defect, the septal occluder comprising:
a proximal anchor member, having an outer surface, axial length and a transverse dimension, and the axial length is longer than the transverse dimension, for deployment at a first end of the septal defect;
a distal anchor member having an outer surface for deployment at a second end of said septal defect; and
a flexible connection layer, having a width and a length, fixedly attached to said proximal anchor member along a proximal attachment line and fixedly attached to said distal anchor member along a distal attachment line, said proximal and distal anchor members and said flexible connection layer comprising one or more bioresorbable materials,
wherein the proximal attachment line extends in an axial direction on the outer surface of the proximal anchor member, the distal attachment line extends in an axial direction on the outer surface of the distal anchor member, and at least one of the distal attachment line and proximal attachment line being along the width of the flexible connection layer.

57. The apparatus of claim 56, wherein at least one of said proximal and distal anchor members is configured to move pivotally relative to said flexible connection layer.

58. An apparatus for closing a septal defect, comprising:
a delivery system including a sheath having a tip positionable at the defect; and
a septal occluder collapsible for delivery through the sheath for deployment at the septal defect, the septal occluder comprising:
an elongated proximal anchor member for deployment at a first end of the septal defect;
an elongated distal anchor member for deployment at a second end of said septal defect; and
a flexible layer having a width and a length, said flexible layer being fixedly attached to said proximal anchor member at a first connection location and fixedly attached to said distal anchor member at a second connection location, wherein at least one of the first and second connection locations forms a juncture line along the width of the flexible layer and along a portion of an axial length of the corresponding anchor member and wherein the flexible layer includes filaments disposed along at least a portion of the axial length of the corresponding anchor member.

59. An apparatus for closing a septal defect, comprising:
a delivery system including a sheath having a tip positionable at the defect; and
a septal occluder collapsible for delivery through the sheath for deployment at the septal defect, the septal occluder comprising:
a proximal anchor member having an outer surface, an axial length and a transverse dimension, the axial length being longer than the transverse dimension, for deployment at a first end of the septal defect;
a distal anchor member for deployment proximate a second end of said septal defect;
a flexible connection layer, having a width and a length, fixedly attached to said proximal anchor along a proximal attachment line extending in an axial direction on the outer surface of the proximal anchor member, and fixedly attached to said distal anchor member along a distal attachment line, wherein at least one of the distal attachment line and proximal attachment line being along the width of the flexible connection layer; and a removal string extending from said proximal anchor member to facilitate collapsing and removal of the occluder from the septal defect into the delivery sheath if desired.

60. The apparatus of claim 59, wherein at least one of said proximal and distal anchor members is configured to move pivotally relative to said flexible connection layer.

61. A septal occluder, comprising:
a proximal anchor member having an outer surface, an axial length and a transverse dimension,
wherein the axial length is larger than the transverse dimension for deployment proximate a first end of a septal defect;
a distal anchor member for deployment proximate a second end of said septal defect; and
a flexible connection layer, having a width and a length, fixedly attached to said proximal anchor member along a proximal attachment line along an axial direction on the outer surface of the proximal anchor member, and fixedly attached to said distal anchor member along a distal attachment line, at least one of the distal attachment line and proximal attachment line being along the width of the flexible connection layer;
said proximal and distal anchor members and said flexible connection layer comprising one or more plastic materials.

62. The septal occluder of claim 61 wherein said proximal and distal anchor members are elongated.

63. The septal occluder of claim 61 wherein said proximal and distal anchor members each have a generally cylindrical shape with rounded ends.

64. The septal occluder of claim 61 wherein a side of each anchor member for contacting a tissue surface is generally flattened to increase surface contact.

65. The septal occluder of claim 61 wherein said proximal and distal anchor members each comprise a cylindrical structure formed by rolling a layer of material.

66. The septal occluder of claim 61 wherein said proximal and distal anchor members are inflatable.

67. The septal occluder of claim 61 wherein said septal occluder is collapsible for passage through a catheter or sheath.

68. The septal occluder of claim 67 wherein said occluder can be collapsed with the proximal and distal anchor members being in a generally aligned, end to end arrangement for passage through a catheter or sheath.

69. The septal occluder of claim 61 wherein said proximal and distal anchor members are collapsible for deployment or removal.

70. The septal occluder of claim 69 wherein the proximal and distal anchor members are generally foldable.

71. The septal occluder of claim 70 wherein each anchor member includes two elements separated by an elastic hinge.

72. The septal occluder of claim 61 further comprising a removal string attached to the septal occluder to facilitate removal of the septal occluder from the septal defect.

73. The septal occluder of claim 72 wherein said removal string is slidingly mounted in said proximal anchor member and attached to said distal anchor member.

74. The septal occluder of claim 72 wherein said removal string is mounted to slide through said proximal anchor member.

75. The septal occluder of claim 72 further comprising a delivery string to facilitate deployment of the septal occluder at the septal defect.

76. The septal occluder of claim 61 wherein said septal occluder is formed from a layer of material having opposite ends rolled to form the proximal and distal anchor members.

77. The septal occluder of claim 61 further comprising a wire connecting said proximal and distal anchor members to provide clamping force to close the defect.

78. The septal occluder of claim 77 wherein said wire has a serpentine configuration.

79. The septal occluder of claim 71 wherein said flexible connection layer comprises a layer of elastomeric material.

80. The septal occluder of claim 61 wherein said flexible connection layer comprises a layer of material made from thrombogenic or inflammatory materials.

81. The septal occluder of claim 61 wherein said flexible connection layer comprises a layer of material that is porous or textured.

82. The septal occluder of claim 61 wherein said flexible connection layer comprises a layer of material that is covered with a biocompatible glue to promote adherence to tissue.

83. The septal occluder of claim 61 wherein said flexible connection layer comprises a layer of material that is covered with growth factors to accelerate tissue ingrowth.

84. The septal occluder of claim 61, wherein at least one of said proximal and distal anchor members is configured to move pivotally relative to said flexible connection layer at least one of the first and second connection locations.

* * * * *